(12) United States Patent
McGrath et al.

(10) Patent No.: US 10,827,917 B2
(45) Date of Patent: Nov. 10, 2020

(54) LARYNGOSCOPES, LARYNGOSCOPE ARMS AND METHODS OF MANUFACTURE

(71) Applicant: Aircraft Medical Limited, Edinburgh (GB)

(72) Inventors: Matthew John Ross McGrath, Edinburgh (GB); Peter Douglas Colin Inglis, Edinburgh (GB)

(73) Assignee: Aircraft Medical Limited, Edinburgh (GB)

( * ) Notice: Subject to any disclaimer, the term of this patent is extended or adjusted under 35 U.S.C. 154(b) by 202 days.

(21) Appl. No.: 16/206,484

(22) Filed: Nov. 30, 2018

(65) Prior Publication Data

US 2019/0142263 A1 May 16, 2019

Related U.S. Application Data

(63) Continuation of application No. 15/088,791, filed on Apr. 1, 2016, now Pat. No. 10,159,405, which is a (Continued)

(30) Foreign Application Priority Data

May 13, 2010 (GB) .................................. 1008021.6
Oct. 13, 2010 (GB) .................................. 1017291.4

(51) Int. Cl.
*A61B 1/267* (2006.01)
*A61B 1/00* (2006.01)
*A61B 1/04* (2006.01)

(52) U.S. Cl.
CPC .......... *A61B 1/267* (2013.01); *A61B 1/00052* (2013.01); *A61B 1/00066* (2013.01);
(Continued)

(58) Field of Classification Search
USPC ........................................................ 600/188
See application file for complete search history.

(56) References Cited

U.S. PATENT DOCUMENTS 5,682,880 A 11/1997 Brain
5,800,344 A * 9/1998 Wood, Sr. .............. A61B 1/267
600/185
(Continued)

FOREIGN PATENT DOCUMENTS

GB 2493895 B 8/2007
GB 2452400 A 4/2009

OTHER PUBLICATIONS

Examination Report (3 pgs.) dated Mar. 18, 2014 in corresponding to UK Application No. GB1222462.2.
(Continued)

*Primary Examiner* — Sameh R Boles
(74) *Attorney, Agent, or Firm* — Fletcher Yoder, P.C.

(57) ABSTRACT

A video laryngoscope has an arm comprising a video camera, at least one electrical conductor extending to the video camera, an elongate electrical conductor retaining member retaining the electrical conductor and an over-moulding extending around the elongate cable retaining member and having a smooth outer surface has the benefit of allowing the laryngoscope arm to be readily cleaned or sterilised, and minimises the number of features, such as seams or joints, where dirt or infectious bodies may be retained.

20 Claims, 5 Drawing Sheets

Related U.S. Application Data continuation of application No. 13/697,608, filed as application No. PCT/GB2011/050922 on May 13, 2011, now Pat. No. 9,314,151.

(52) U.S. Cl.
CPC ...... *A61B 1/00078* (2013.01); *A61B 1/00124* (2013.01); *A61B 1/04* (2013.01); *Y10T 29/49002* (2015.01)

(56) References Cited

U.S. PATENT DOCUMENTS

| | | |
|---|---|---|
| 2007/0167686 A1 | 7/2007 | McGrath |
| 2007/0299313 A1 | 12/2007 | McGrath |
| 2009/0032016 A1 | 2/2009 | Law et al. |
| 2009/0299146 A1 | 12/2009 | McGrath |
| 2010/0256451 A1 | 10/2010 | McGrath |
| 2010/0312059 A1 | 12/2010 | McGrath |
| 2012/0059223 A1 | 3/2012 | McGrath et al. |
| 2012/0065471 A1 | 3/2012 | McGrath et al. |
| 2012/0095294 A1 | 4/2012 | McGrath et al. |
| 2012/0095295 A1 | 4/2012 | McGrath et al. |
| 2013/0060090 A1 | 3/2013 | McGrath et al. |
| 2014/0121463 A1 | 5/2014 | McGrath et al. |

OTHER PUBLICATIONS

International Search Report for PCT/GB2011/050922, dated Aug. 4, 2011, 2 pages.

\* cited by examiner

LARYNGOSCOPES, LARYNGOSCOPE ARMS AND METHODS OF MANUFACTURE

CROSS REFERENCE TO RELATED APPLICATIONS

This application is a continuation of U.S. patent application Ser. No. 15/088,791, filed on Apr. 1, 2016, which is a continuation of U.S. patent application Ser. No. 13/697,608, (patented as U.S. Pat. No. 9,314,151), filed on Nov. 13, 2012 which is the U.S. national phase of International Application No. PCT/GB2011/050922, filed May 13, 2011, which claims priority to GB Patent Application No. 1008021.6, filed May 13, 2010, and GB Patent Application No. 1017291.4 filed Oct. 13, 2010, which are incorporated herein by reference in their entirety.

FIELD OF THE INVENTION

The present invention relates to the field of laryngoscopes, including video laryngoscopes, and in particular to the field of laryngoscope arms, and methods of manufacturing laryngoscope arms.

BACKGROUND TO THE INVENTION

Laryngoscopes are medical devices which are employed to introduce endotracheal tubes into patient's airways, for example, when a patient is being anaesthetised.

Laryngoscopes comprise handles and arms. Within the specification, the term laryngoscope arm is used to refer to the part of the laryngoscope which extends from the handle into the patient's mouth in use.

Laryngoscope handles are usually elongate and are typically arranged at an angle to the proximal end of the laryngoscope arm. However, in some known laryngoscopes, the handle is arranged parallel or approximately parallel to the proximal end of the arm.

In some known laryngoscopes, the laryngoscope arm functions as a laryngoscope blade. The term laryngoscope blade is used within the specification to refer to the part of the laryngoscope which in use contacts the patient and lifts the tissue adjacent to the epiglottis, to enable a view of the patient's larynx to be obtained during intubation.

In other known embodiments, the laryngoscope arm functions to retain a laryngoscope blade, particularly a disposable laryngoscope blade.

Laryngoscopes typically comprise at least two parts, resulting in gaps and joins when they are assembled. Microbes may collect and proliferate in such spaces and such spaces may be hard to clean. Therefore, it may be difficult to adequately sterilise such laryngoscopes after use without fully disassembling them. Furthermore, the more locations on the surface of a laryngoscope or part of a laryngoscope, such as a laryngoscope arm, in which microbes may aggregate, the harder it will be to adequately sterilise the laryngoscope or part of the laryngoscope.

It would therefore be advantageous to provide laryngoscopes and parts for laryngoscopes, such as laryngoscope arms, having a surface with fewer locations in which microbes may aggregate, since it would be easier to adequately sterilise such laryngoscopes or parts thereof, between use. It would also be advantage to provide a method of manufacturing such laryngoscopes and parts for such laryngoscopes, including laryngoscope arms.

One of the reasons why laryngoscopes, including video laryngoscopes, typically comprise at least two parts is to enable electrical wires or fibre-optic bundles to be run through the laryngoscope or a part of the laryngoscope such as a laryngoscope arm.

As discussed above, it may be harder to adequately sterilise laryngoscopes comprising at least two parts. Therefore, it would be advantageous to provide laryngoscopes and parts of laryngoscopes, such as laryngoscope arms, having a surface with fewer locations in which microbes may aggregate but through which electrical wires or fibre-optic bundles can be run. It would also be advantageous to provide a method of manufacturing such laryngoscopes and parts for such laryngoscopes, including laryngoscope arms.

As mentioned above, a laryngoscope arm may function as a laryngoscope blade or may retain a laryngoscope blade. Laryngoscope blades must be able to withstand significant forces as they lift and manipulate a patient's tissue adjacent the epiglottis to enable a view of the larynx to be obtained. However, the bulkier the blade, the more difficult it will be obtain a clear view of the larynx or to manoeuvre the blade and the greater the chance of damaging the patient's teeth. Therefore, some aspects of the invention aim to provide a strong laryngoscope whilst minimising the bulk of the blade.

SUMMARY OF THE INVENTION

According to a first aspect of the invention there is presented a laryngoscope arm comprising a video camera, at least one electrical conductor extending to the video camera, an elongate electrical conductor retaining member retaining the electrical conductor and an overmoulding extending around the elongate conductor retaining member and having a smooth outer surface.

Preferably, the elongate electrical conductor retaining member acts as a strengthening element. The elongate electrical conductor retaining member may form a structural chassis for the laryngoscope arm.

Providing a laryngoscope arm overmoulded to provide a smooth outer surface has the benefit of allowing the laryngoscope arm to be readily cleaned or sterilised, and minimises the number of features, such as seams or joints, where dirt or infectious bodies may be retained. The overmoulding typically forms the outside surface of the majority or all of the laryngoscope arm. The overmoulding typically has a smooth outer skin, providing structural integrity, avoiding features which may retain dirt and providing comprehensive sealing.

Preferably, the elongate conductor retaining member is an open channel. The elongate conductor retaining member may be manufactured by pressing sheet material (such as sheet metal) into the required form. Pressing is a simple and cost effective method of manufacture. Accordingly, a laryngoscope arm comprising an open channel elongate conductor retaining member has the benefit of being cheaper to manufacture whilst retaining the mechanical strength provided by the elongate conductor retaining member.

Alternatively, the elongate conductor retaining member may be tubular. A tubular form may provide a greater structural integrity to the laryngoscope arm than an open channel form. It may also leave a tubular space through which one or more electrical conductors (and in some cases optical fibres) can be threaded after overmoulding.

The tubular elongate conductor retaining member may be blow moulded metal. The tubular elongate conductor retaining member may be hydro-formed metal.

Within this specification and the appended claims, by 'overmoulding' we include 'overcasting' (of metal). The overmoulding may be a metal, such as aluminium, zinc or titanium, for example. Alternatively, the overmoulding may be formed of a plastics material such as polyethylene or polyamide, for example. The plastics material may be a structured polymer such as block polymers, for example.

The laryngoscope arm may comprise a strengthening element. The strengthening element may comprise an elongate element. The elongate element may be generally planar. The elongate element may extend along at least 50 percent of the laryngoscope arm, preferably along at least 70 percent of the laryngoscope arm and more preferably along at least 90 percent of the laryngoscope arm.

Preferably, the elongate element is formed from a sheet material, such as sheet metal. The elongate element may be generally planar. The generally planar elongate element may comprise a major plane. The generally planar elongate element may be oriented within the laryngoscope arm such that the major plane of the generally planar elongate element is parallel to the force vector generally applied to the laryngoscope arm during use such that it may provide greater resistance to such forces.

The generally planar elongate element may support electrical conductors running along the length of the generally planar elongate conductor retaining member.

The generally planar elongate element may comprise a printed circuit board (PCB). Alternatively, the electrical conductors running the length of the generally planar elongate conductor retaining member may comprise a PCB. The PCB may comprise a battery.

The laryngoscope arm may comprise a plurality of strengthening elements. The plurality of strengthening elements may be a plurality of elongate elements. The plurality of elongate elements may be generally planar. Each of the plurality of elongate elements may comprise a major plane. Each elongate element within the plurality of elongate elements may be arranged such that the major planes of the elongate elements are generally parallel. Alternatively, the elongate elements may be arranged such that the major planes of the elongate elements intersect. For example, in cross section, the elongate elements may form a geometric shape such as a triangle (for three elongate elements) or rectangle (for four elongate elements). One or more of the plurality of elongate elements may comprise a PCB.

The overmoulding may extend around the elongate conductor retaining member such that the overmoulding has the same general cross-sectional profile as the elongate conductor retaining member. For example, the overmoulding extending around an elongate conductor retaining member having a square cross-section may have a generally square cross-section.

The overmoulding may comprise an extended portion extending in one dimension substantially beyond the elongate conductor retaining member or strengthening element. The extended portion may comprise at least one electrical conductor. The at least one electrical conductor may be entirely or partially enclosed within the extended portion. The cross-section of the extended portion may span the cross-section of the elongate conductor retaining member. The cross-section of the extended portion may partially span the cross-section of the elongate conductor retaining member.

The overmoulding may have a cross-sectional profile that is substantially independent of the cross-sectional profile of the elongate conductor retaining member. The overmoulding may comprise a feature such as a channel, for example, that is independent of the elongate conductor retaining member and/or strengthening element.

Preferably, the laryngoscope arm comprises a light source and the at least one electrical conductor extends to the light source. Preferably, the light source is integral to the laryngoscope arm, but may be detachable from the laryngoscope arm. For example, the light source may be a detachable light emitting diode (LED).

Preferably, the laryngoscope arm comprises at least two electrical conductors such that at least one electrical conductor extends to the video camera and at least one electrical conductor extends to the light source.

The provision of a light source in the laryngoscope arm allows the target of the video camera within the laryngoscope arm to be illuminated such that at least adequate light reflected from the target reaches the video camera. Therefore, the provision of an integrated light source allows an endotracheal tube to be accurately positioned whilst the laryngoscope arm is inserted into the patient's mouth and throat.

The laryngoscope arm may be a laryngoscope blade, e.g. by virtue of having an outer surface in the shape of a laryngoscope blade. The laryngoscope blade may comprise tube guiding members operable to guide an endotracheal tube to the end of the laryngoscope blade and in some embodiments to demountably retain an endotracheal tube before and during advancement through the larynx. The laryngoscope blade may be generally spatulate.

Alternatively, the laryngoscope arm may comprise a demountable sleeve retaining formation. The demountable sleeve retaining formation may receive a sleeve, such as a demountable laryngoscope blade having a channel into which the arm may fit, for example. A clip may be provided to retain a demountable sleeve. The demountable laryngoscope blade may be generally spatulate and comprise a channel having a transparent end face. The laryngoscope arm may be inserted into the channel of the demountable laryngoscope blade such that the demountable laryngoscope blade may extend along at least seventy five percent of the length of the laryngoscope arm. The sleeve (e.g. demountable laryngoscope blade) may be disposable. The laryngoscope arm may be reusable. Thus, the part which contacts the patient's body in use (the sleeve) is disposed of and the remaining parts of the device, including the laryngoscope arm, can be cleaned. Due to the smooth nature of overmoulded surfaces, the arm can be readily cleaned.

The cross-sectional profile of the channel of the demountable laryngoscope blade may correspond to a keying feature. The cross-sectional profile of the overmoulding may comprise a keying feature. The keying feature of the overmoulding may be complimentary to the keying feature of the channel of the demountable laryngoscope blade.

According to a second aspect of the invention there is presented a laryngoscope arm comprising a video camera, at least one electrical conductor extending to the video camera and an overmoulding having a smooth outer surface.

Providing a laryngoscope arm overmoulded to provide a smooth outer surface has the benefit of allowing the laryngoscope arm to be readily cleaned or sterilised, and minimises the number of features, such as seams or joints, where dirt or infectious bodies may be retained. The overmoulding typically forms the outside surface of the majority or all of the laryngoscope arm. The overmoulding typically has a smooth outer skin, providing structural integrity, avoiding features which may retain dirt and providing comprehensive sealing.

The laryngoscope arm may comprise a strengthening element. The overmoulding may extend around the strengthening element. The strengthening element may extend along at least 50 percent of the laryngoscope arm, preferably along at least 70 percent of the laryngoscope arm and more preferably along at least 90 percent of the laryngoscope arm.

The strengthening element may comprise a plurality of elongate elements. The plurality of elongate elements may be generally planar. Each of the plurality of elongate elements may comprise a major plane. Each elongate element within the plurality of elongate elements may be arranged such that the major planes of the elongate elements are generally parallel. Alternatively, the elongate elements may be arranged such that the major planes of the elongate elements intersect. For example, in cross section, the elongate elements may form a geometric shape such as a triangle (for three elongate elements) or rectangle (for four elongate elements).

One or more of the plurality of elongate elements may comprise a PCB.

The strengthening element may form a structural chassis for the laryngoscope arm.

The overmoulding may extend around the strengthening element such that the overmoulding has the same general cross-sectional profile as the elongate conductor retaining member. For example, the overmoulding may form a uniform protective layer around the strengthening element.

The overmoulding may comprise an extended portion extending in one dimension substantially beyond the strengthening element. The extended portion may comprise at least one electrical conductor. The at least one electrical conductor may be entirely or partially enclosed within the extended portion. The cross-section of the extended portion may span the cross-section of the strengthening element. The cross-section of the extended portion may partially span the cross-section of the strengthening element.

The overmoulding may have a cross-sectional profile that is substantially independent of the cross-sectional profile of the strengthening element. The overmoulding may comprise a feature such as a channel, for example, that is independent of the strengthening element.

Preferably, the laryngoscope arm comprises a light source and the at least one electrical conductor extends to the light source. Preferably, the light source is integral to the laryngoscope arm, but may be detachable from the laryngoscope arm. For example, the light source may be a detachable light emitting diode (LED).

Preferably, the laryngoscope arm comprises at least two electrical conductors such that at least one electrical conductor extends to the video camera and at least one electrical conductor extends to the light source. At least one electrical conductor may comprise a PCB.

The provision of a light source in the laryngoscope arm allows the target of the video camera within the laryngoscope arm to be illuminated such that at least adequate light reflected from the target reaches the video camera. Therefore, the provision of an integrated light source allows an endotracheal tube to be accurately positioned whilst the laryngoscope arm is inserted into the patient's mouth and throat.

The laryngoscope arm may be a laryngoscope blade, e.g. by virtue of having an outer surface in the shape of a laryngoscope blade. The laryngoscope blade may comprise tube guiding members operable to guide an endotracheal tube to the end of the laryngoscope blade and in some embodiments to demountably retain an endotracheal tube before and during advancement through the larynx. The laryngoscope blade may be generally spatulate.

Alternatively, the laryngoscope arm may comprise a demountable sleeve retaining formation. The demountable sleeve retaining formation may receive a sleeve, such as a demountable laryngoscope blade having a channel into which the arm may fit, for example. A clip may be provided to retain a demountable sleeve. The demountable laryngoscope blade may be generally spatulate and comprise a channel having a transparent end face. The laryngoscope arm may be inserted into the channel of the demountable laryngoscope blade such that the demountable laryngoscope blade may extend along at least seventy five percent of the length of the laryngoscope arm. The sleeve (e.g. demountable laryngoscope blade) may be disposable. The laryngoscope arm may be reusable. Thus, the part which contacts the patient's body in use (the sleeve) is disposed of and the remaining parts of the device, including the laryngoscope arm, can be cleaned. Due to the smooth nature of overmoulded surfaces, the arm can be readily cleaned.

The cross-sectional profile of the channel of the demountable laryngoscope blade may correspond to a keying feature. The cross-sectional profile of the overmoulding may comprise a keying feature. The keying feature of the overmoulding may be complimentary to the keying feature of the channel of the demountable laryngoscope blade.

According to a third aspect of the invention there is presented a video laryngoscope comprising a body and a laryngoscope arm according to the first or second aspects of the invention.

Providing a video laryngoscope having an arm overmoulded to provide a smooth outer surface has the benefit of allowing the video laryngoscope to be readily cleaned or sterilised, and minimises the number of features, such as seams or joints, where dirt or infectious bodies may be retained.

Preferably, the body comprises a handle support integral with the elongate conductor retaining member and a handle overmoulded on the handle support.

The integral handle support and elongate conductor retaining member may act as a strengthening element for the video laryngoscope.

The laryngoscope may be provided in a kit further comprising a demountable sleeve, such as a laryngoscope blade, demountably retainable by the laryngoscope arm.

According to a fourth aspect of the invention there is presented a method of forming a laryngoscope arm comprising a video camera and one or more electrical conductors, the method comprising providing an elongate conductor retaining member, overmoulding a covering material around the elongate conductor retaining member forming a smooth outer surface.

One or more electrical conductors (typically extending to the video camera) may be provided in the elongate conductor retaining member prior to the step of overmoulding. One or more electrical conductors (typically extending to the video camera) may be threaded through the elongate conductor retaining member after the step of overmoulding. At least one of the one or more electrical conductors may be part of a PCB. Thus, the method may comprise providing a PCB comprising at least one (and optionally each) of the electrical conductors.

The elongate conductor retaining member may be tubular. The step of forming the elongate conductor retaining member may comprise the step of blow moulding a metal tube. A tubular elongate conductor retaining member facilitates the threading of one or more electrical conductors after the step of overmoulding.

The elongate conductor retaining member may be an open channel. The step of forming the elongate conductor retaining member may comprise the step of pressing a deformable sheet material.

Preferably, the overmoulded covering material is a metal such as aluminium, zinc or titanium, for example. Alternatively, the overmoulded covering material is a plastics material such as polyethylene or polyamide, for example. The plastics material may comprise a structured plastic.

According to a fifth aspect of the invention there is provided a method of forming a laryngoscope comprising a body and an arm wherein the arm is formed according to the method of the third aspect of the invention above.

Preferably, the body comprises a handle support, integral with the elongate conductor retaining member, and the method further comprises overmoulding a handle onto the handle support.

Preferably the handle support and elongate conductor retaining member comprise a single metal piece forming a chassis for the laryngoscope. The chassis may be a strengthening element such that the laryngoscope arm may withstand the forces subjected to it during use.

Preferably, the chassis comprises a recess. The recess may be associated with the handle support and may form a chamber adapted to retain a body such as a battery or a series of batteries, for example. Alternatively, the recess may form a chamber adapted to retain a chemical agent such as lidocaine, for example. The chamber may be adapted such that the chemical agent may be applied through the laryngoscope arm, for example.

According to a sixth aspect of the invention there is provided a method of forming an arm for a laryngoscope comprising the steps of providing a metal tube within a mould and passing high pressure fluid through the metal tube such that the metal tube expands to fill the mould.

A mould support may be provided to support the mould during the method. The mould support may be demountable after the arm is formed.

Preferably, the fluid is a liquid, such as water, for example. Alternatively, the fluid may be a gas such as air, for example.

The metal tube may comprise at least one seal such that at least one end of the metal tube may be sealed. Typically, the seal is of sufficient strength to withstand the pressure applied by the high pressure fluid.

The invention extends in a seventh aspect to a video laryngoscope comprising a video camera and a printed circuit board, the printed circuit board comprising control electronics to control the function of the video laryngoscope and an electrical conductor supplying power to the camera, and an overmoulding extending around the elongate conductor retaining member and having a smooth outer surface.

Typically, the video laryngoscope comprises a body and a laryngoscope arm extending from the body. The overmoulding may define at least part, or at least the majority, or all, of the body. The overmoulding may define at least part, at least the majority, or all, of the laryngoscope arm.

The printed circuit board therefore functions to retain control electronics, provide power to the camera and provide mechanical support to the laryngoscope arm, which resists the substantial bending forces acting on the laryngoscope during intubation (particularly while raising the tissue adjacent the epiglottis to obtain a view of the larynx).

The camera may be mounted to the printed circuit board. There may be a further electrical conductor extending from the said electrical conductor to connect the camera to the printed circuit board.

The video laryngoscope may comprise a screen for displaying video images. The video laryngoscope may comprise a video output for outputting video data to a remote screen.

The printed circuit board is preferably oriented parallel to a plane including a central axis of the body and a central axis of the laryngoscope arm, that is to say the plane which will be parallel to a patient's mid-sagittal plane during operation.

According to an eighth aspect of the invention there is presented a method of forming a video laryngoscope according to the seventh aspect of the invention, the method comprising providing a printed circuit board, the printed circuit board comprising control electronics to control the function of a video laryngoscope, and overmoulding a covering material around the printed circuit board forming a smooth outer surface.

Optional features described above in relation to any one of the first through eighth aspects of the invention are optional features of each of the first through eighth aspects of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1A:
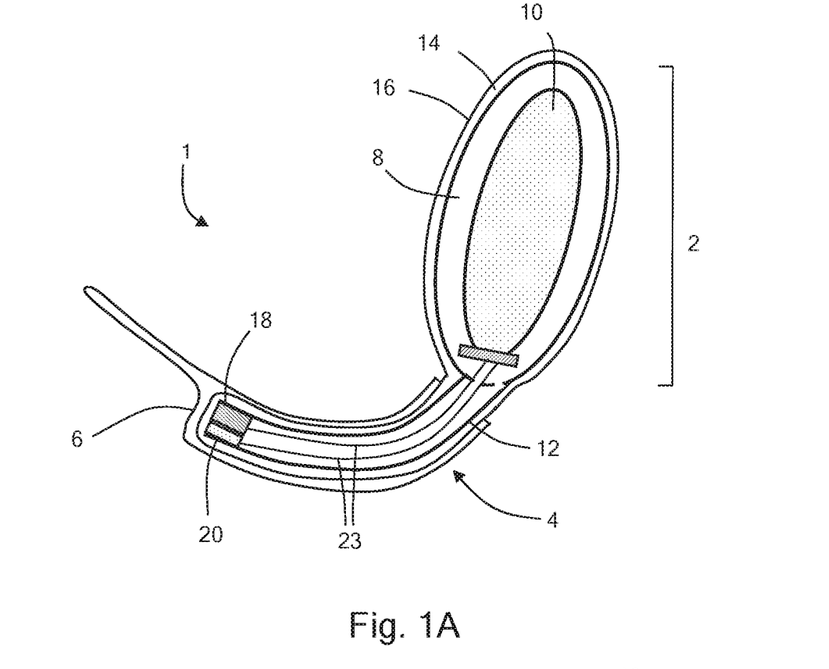
FIG. 1A is a section view of a laryngoscope.
Figure 1B:
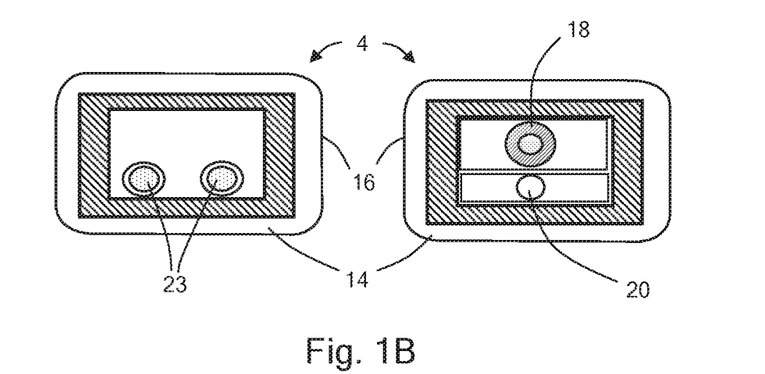
FIG. 1B is a section view of a laryngoscope arm.
Figure 2:
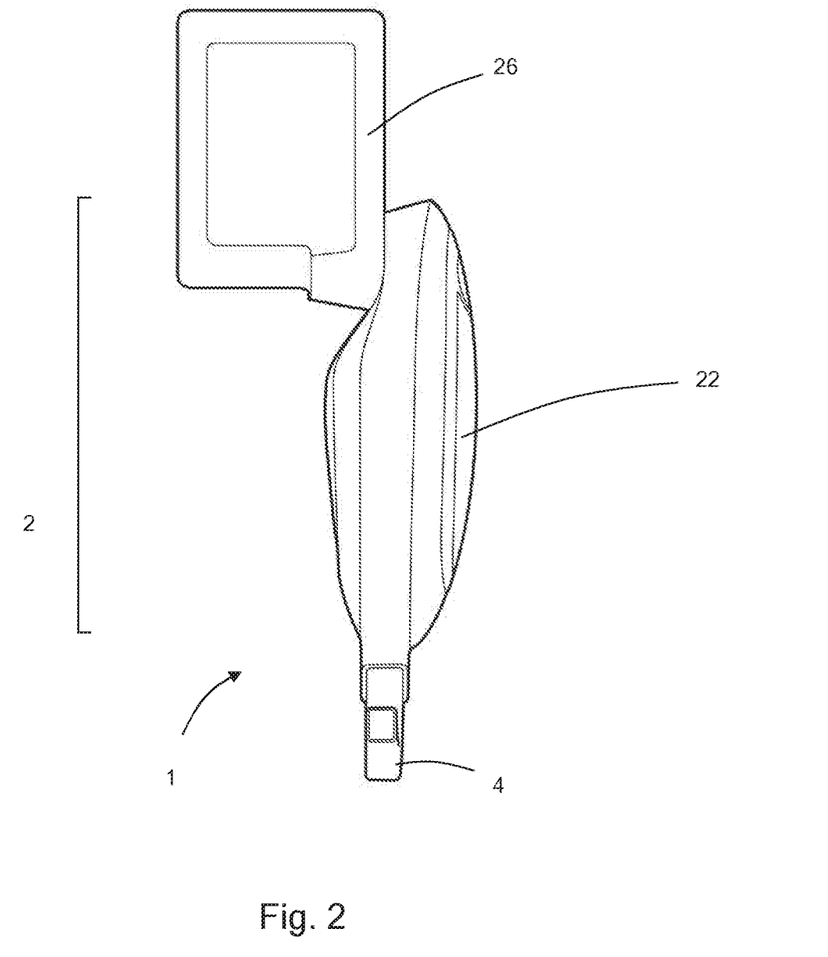
FIG. 2 frontal plan view of a video laryngoscope.
Figure 3A:
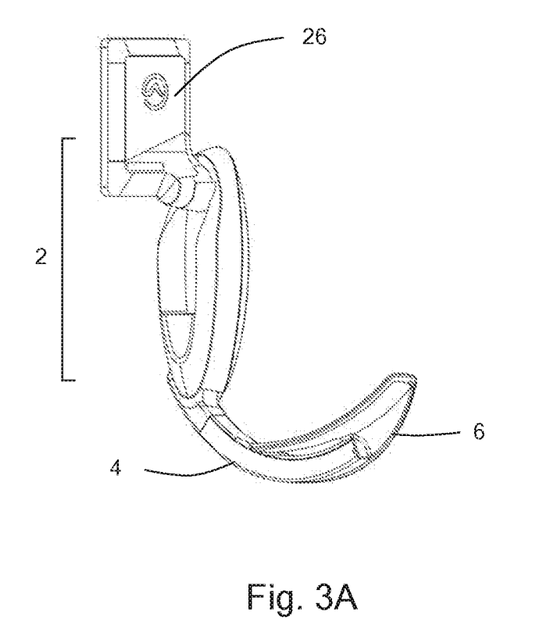
FIG. 3A is a perspective view of a video laryngoscope.
Figure 3B:
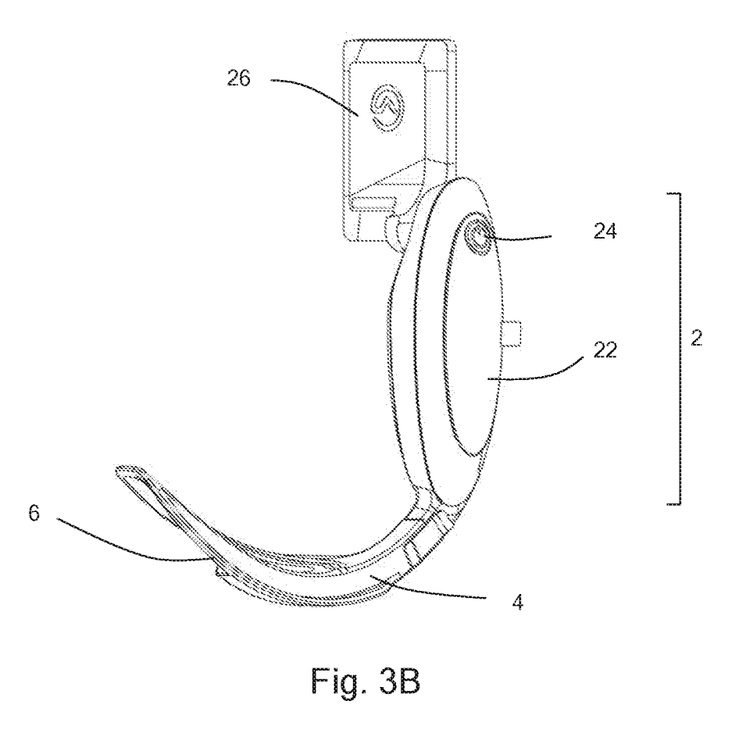
FIG. 3B is a perspective view of a video laryngoscope.
Figure 4A:
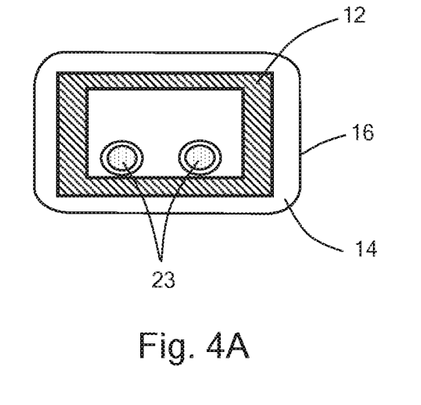
FIG. 4A is a section view of an embodiment of a laryngoscope arm.
Figure 4B:
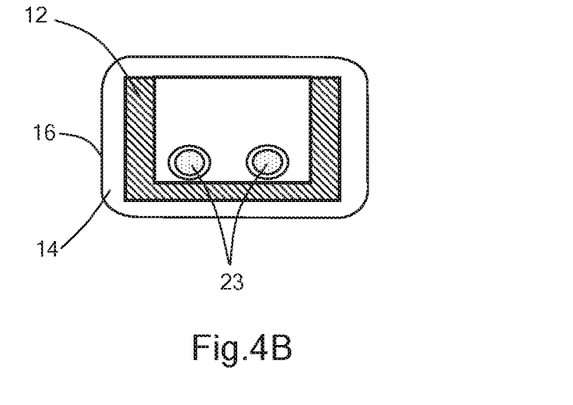
FIG. 4B is a section view of an embodiment of a laryngoscope arm.
Figure 4C:
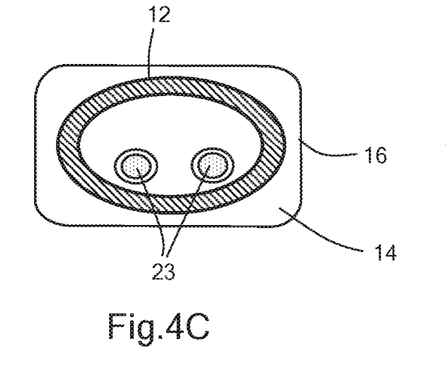
FIG. 4C is a section view of an embodiment of a laryngoscope arm.
Figure 4D:
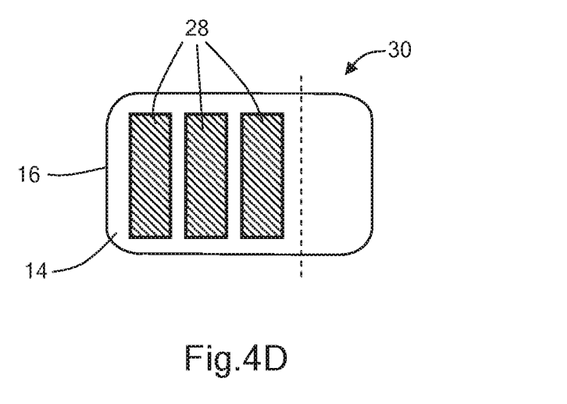
FIG. 4D is a section view of an embodiment of a laryngoscope arm.
Figure 4E:
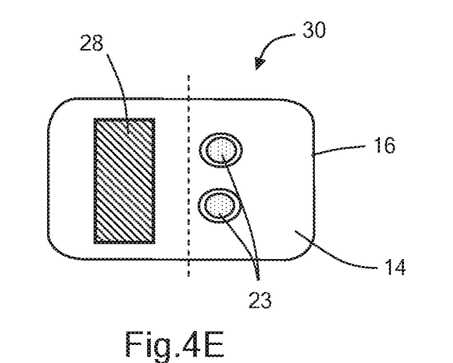
FIG. 4E is a section view of an embodiment of a laryngoscope arm.
Figure 4F:
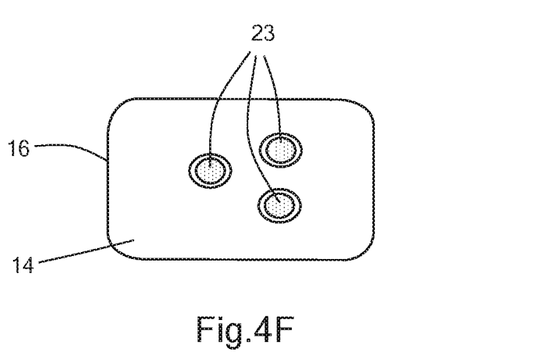
FIG. 4F is a section view of an embodiment of a laryngoscope arm.
Figure 5A:
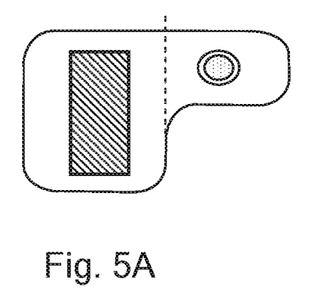
FIG. 5A is a section view of an embodiment of a laryngoscope arm.
Figure 5B:
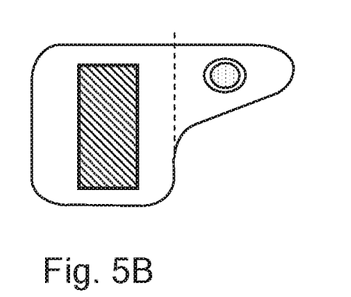
FIG. 5B is a section view of an embodiment of a laryngoscope arm.
Figure 5C:
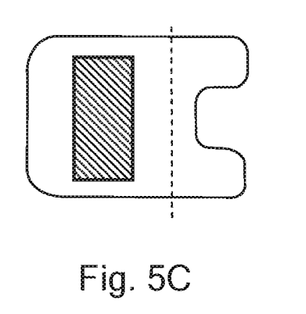
FIG. 5C is a section view of an embodiment of a laryngoscope arm.

With reference to FIGS. 1 to 3 a video laryngoscope 1 comprises a body 2 and an arm 4. The video laryngoscope is typically used with a demountable transparent rigid plastics sheath 6, functioning as a laryngoscope blade.

The laryngoscope comprises a chassis formed by a metal loop 8 within the body, which has a central aperture providing a space for electronics 10, batteries and so forth, and a metal tube 12 which extends from the metal loop. The metal loop functions as a strengthening element for the body and the metal tube functions as a strengthening element for the arm.

The chassis is covered with an overmould 14 of a plastics material. The overmould has a smooth outer surface 16. In this example, the overmould is continuous over both the handle and arm, however, this may not be the case.

The arm also includes a video camera 18 and a light 20 (typically and LED), which may be attached to the end of the overmould, behind a suitable transparent cover, or included in a part of the metal tube and so also covered, in part, by the overmould.

The body includes a demountable battery pack 22, which is recessed into the space within the metal loop, an activation switch 24 and a video screen 26.

Electrical wires 23 connecting the electronics, battery pack and video screen run within the body and along the interior of the metal tube.

The chassis provides structural integrity. The metal tube ensures that the arm is strong and will not break in use while protecting the electrical conductors. The overmould provides a smooth outer surface which can be readily cleaned, enabling the laryngoscope to be used with one patient and then reused with another patient, after the disposable blade has been replaced and the laryngoscope has been cleaned. The smooth surface, without the joins that would arise from convential multi-part constructions facilitates cleaning.

The video laryngoscope is fabricated by forming the chassis and then forming the overmould over the chassis. The electrical wires running between the electronics and the light and camera can then be threaded through the metal tube, which functions as an electrical conductor retaining member. The video camera and light may be present before or after the overmoulding step.

In an alternative embodiment, the overmoulding of the largnoscope arm may be formed as laryngoscope blade, providing a one piece device. Such a device may be disposable after one or a limited number of uses.

In this example, the overmoulding on the handle and the arm are continuous. However, they may be formed separately. The chassis may be unitary, with the metal tube joined to the metal loop. However, they may be separate parts and the structure of the chassis can be designed as required.

In some embodiments, the overmoulded material is a metal, such as zinc or aluminium. This is especially helpful where the arm may be cleaned many times, or needs to be cleaned stringently, or is formed as a laryngoscope blade and intended for single or limited use.

The metal tube need not be enclosed. In a cost effective embodiment, the laryngoscope arm includes an open channel formed by pressing an elongate sheet of metal, which retains one or more conductors. An electrical signal may be transmitted through the metal of the elongate conductor retaining member.

In an alternative embodiment the arm comprises a strengthening element 28 in the place of the metal tube of the previous embodiment. The strengthening element comprises a planar elongate element. The overmoulding extends around the strengthening element. A portion 30 of the cross-sectional profile of the overmoulding extends beyond the cross-sectional profile of the strengthening element. The portion comprises electrical wires running through the length of the arm.

In further alternative embodiments, the strengthening element comprises a printed circuit board. The printed circuit board typically includes control electronics to control the function of the laryngoscope (e.g. a microcontroller) and provides power to the video. A battery and video camera can also be mounted on the printed circuit board, or connected to the printed circuit board using wired connections, whereupon the body and laryngoscope arm can be formed by an overmoulding. This provides an inexpensive simple disposable laryngoscope in which the printed circuit board provides mechanical strength for the laryngoscope arm.

Further variation and modifications may be considered by one skilled in the art, within the scope of the invention herein disclosed.

The invention claimed is:

1. A video laryngoscope, comprising:
 a body comprising a proximal end and a distal end;
 a laryngoscope arm coupled to the body and extending from the distal end, wherein the laryngoscope arm comprises a strengthening element, and a tubular element comprising an electrical conductor coupled to a video camera; and
 an overmoulding extending around the body, wherein the overmoulding has a smooth outer surface.

2. The video laryngoscope of claim 1, wherein the strengthening element extends along at least between 50 percent and 90 percent of the laryngoscope arm.

3. The video laryngoscope of claim 1, wherein the overmoulding at least partially covers the laryngoscope arm.

4. The video laryngoscope of claim 1, wherein the video camera is positioned at or near a terminus of the laryngoscope arm.

5. The video laryngoscope of claim 1, comprising a light source disposed adjacent to the video camera.

6. The video laryngoscope of claim 1, comprising a video screen coupled to the body and disposed adjacent to the proximal end of the body.

7. The video laryngoscope of claim 1, wherein the laryngoscope arm is a laryngoscope blade.

8. The video laryngoscope of claim 1, comprising a demountable laryngoscope blade removably coupled to the laryngoscope arm.

9. The video laryngoscope of claim 1, comprising a chamber configured to apply a chemical agent through the laryngoscope arm.

10. A video laryngoscope, comprising:
 a body;
 a laryngoscope arm comprising a proximal end, a distal end, and a tubular element, wherein the laryngoscope arm is coupled to the body at the proximal end, and wherein the tubular element comprises an electrical conductor;
 a strengthening element extending along at least a portion of the laryngoscope arm;
 a video camera positioned adjacent to the distal end of the laryngoscope arm and coupled to the electrical conductor; and
 an overmoulding extending around the body and at least partially around the laryngoscope arm, wherein the overmoulding has a smooth outer surface.

11. The video laryngoscope of claim 10, wherein the overmoulding comprises an extended portion extending in at least one dimension beyond the strengthening element.

12. The video laryngoscope of claim 11, wherein the tubular element is positioned within the extended portion.

13. The video laryngoscope of claim 10, wherein the laryngoscope arm is a blade, and wherein the blade comprises tube guiding members configured to guide an endotracheal tube to the distal end of the laryngoscope arm.

14. The video laryngoscope of claim 10, comprising a demountable laryngoscope blade removably coupled to the laryngoscope arm.

15. The video laryngoscope of claim 10, wherein the strengthening element extends along at least between 50 percent and 90 percent of the laryngoscope arm.

16. The video laryngoscope of claim 10, comprising a chamber configured to apply a chemical agent through the laryngoscope arm.

17. A video laryngoscope, comprising
- a body having a proximal end and a distal end;
- a laryngoscope arm coupled to and extending from the distal end of the body, wherein the laryngoscope arm comprises a retaining element extending along at least a portion of the laryngoscope arm, a video camera, and a light source, wherein the retaining element comprises an electrical conductor, and wherein at least one of the video camera or the light source is coupled to the electrical conductor;
- a strengthening element extending along or within at least a portion of the laryngoscope arm;
- a video screen coupled to the body and positioned adjacent to the proximal end of the body; and
- an overmoulding extending around the body and at least a portion of the laryngoscope arm such that the overmoulding at least partially covers the strengthening element, wherein the overmoulding has a smooth outer surface.

18. The video laryngoscope of claim 17, wherein the overmoulding comprises an extended portion extending in at least one dimension beyond the strengthening element.

19. The video laryngoscope of claim 18, wherein the retaining element is positioned within the extended portion.

20. The video laryngoscope of claim 17, wherein the laryngoscope arm is a blade, and wherein the blade comprises tube guiding members configured to guide an endotracheal tube.

* * * * *